| United States Patent [19] | [11] Patent Number: 4,510,099 |
|---|---|
| Stern | [45] Date of Patent: Apr. 9, 1985 |

[54] PROCESS FOR PREPARING PURE DIACETONITRILE

[75] Inventor: Gerhard Stern, Linz, Austria

[73] Assignee: Chemie Linz Aktiengesellschaft, Linz, Austria

[21] Appl. No.: 523,623

[22] Filed: Aug. 15, 1983

[30] Foreign Application Priority Data

Aug. 20, 1982 [DE] Fed. Rep. of Germany ....... 3231052

[51] Int. Cl.$^3$ ............................................ C07C 121/45
[52] U.S. Cl. ............................................. 260/465.5 R
[58] Field of Search ................................. 260/465.5 R

[56] References Cited

U.S. PATENT DOCUMENTS 3,290,355 12/1966 Kunisch et al. .............. 260/465.5 R

OTHER PUBLICATIONS

Homer Adkins et al, Am. Soc. 64, pp. 150–154, (1942).

*Primary Examiner*—Joseph Paul Brust
*Attorney, Agent, or Firm*—Mark Dryer

[57] ABSTRACT

Acetonitrile and molten sodium are reacted at a temperature of 96°–140° C. in the presence of an organic solvent which is inert to sodium, to give the sodium salt of diacetonitrile, the salt is hydrolyzed with water, the aqueous and the solvent phases are separated off, and very pure diacetonitrile crystallizes out in cold water.

6 Claims, No Drawings

PROCESS FOR PREPARING PURE DIACETONITRILE

The invention relates to a process for preparing pure diacetonitrile from acetonitrile and molten sodium.

Diacetonitrile, also known as 3-aminocrotonitrile, can be prepared by a known two-stage reaction from acetonitrile and sodium and subsequent decomposition of the sodium salt formed. Leaving aside the possible cis/trans isomeric and tautomeric forms, the reaction can be described by the following equations:

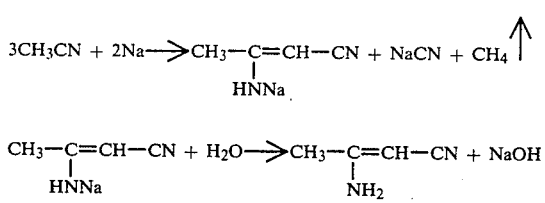

$$1.\quad 3CH_3CN + 2Na \rightarrow \underset{\underset{HNNa}{|}}{CH_3-C=CH-CN} + NaCN + CH_4\uparrow$$

$$2.\quad \underset{\underset{HNNa}{|}}{CH_3-C=CH-CN} + H_2O \rightarrow \underset{\underset{NH_2}{|}}{CH_3-C=CH-CN} + NaOH$$

According to Homer Adkins, Am. Soc. 64, pages 150–154 (1942), the reaction of acetonitrile and sodium is effected with cooling from the outside in benzene under reflux conditions, and the salts formed, namely sodium cyanide and sodium aminocrotonitrile, are filtered off, are suspended in ether, and are slowly decomposed with water. Crude diacetonitrile crystallizes out in a 65% yield from the etherial solution separated off and is then recrystallized from benzene.

According to U.S. Pat. No. 3,290,355, it is unfavorable to work under reflux conditions, and for this reason the condensation of acetonitrile and sodium takes place at a temperature of 10°–35° C. in a relatively high-boiling aliphatic hydrocarbon. To hydrolyze the sodium salt, enough water is slowly added for the temperature not to exceed 40° C. Three layers are formed in the reactor—a hydrocarbon layer at the top, a diacetonitrile and acetonitrile layer in the middle, and an aqueous sodium cyanide and sodium hydroxide layer at the bottom, and the diacetonitrile is isolated from the middle layer. Concerning the isolation of diacetonitrile, this U.S. patent merely states that fractionation takes place.

The main problems in the two processes are due to the use of solid sodium for the highly exothermic condensation reaction. Solid sodium immediately forms at its surface the sodium salt of diacetonitrile, in accordance with reaction equation (1). Since this inorganic salt is insoluble in the surrounding organic medium, an impermeable, firmly adhering crust forms on the metal surface and largely suppresses any further reaction of the metallic sodium. The length of reaction is accordingly for the first stage alone, both on the one liter scale used by Adkins and in the 100 liter scale of U.S. Pat. No. 3,290,355, two to two and a half hours, and the space-time yield is consequently extremely poor and economically unfavorable.

Also the problems of the second reaction stage, namely decomposition of the sodium salt to give free diacetonitrile, are due to the salt crust and the presence of small, unconverted sodium particles, for which reason the addition of water to decompose the sodium salts has to take place with precautions and very slowly, namely in the course of about 2 hours, according to U.S. Pat. No. 3,290,355.

The chief disadvantage however, of the existing methods is that it is impossible to obtain very pure diacetonitrile without repeated recrystallizations, for U.S. Pat. No. 3,290,355, for example, says that a 95% pure product is formed, while according to Adkins it is a crude product. Such degrees of purity, however, are completely unsuitable for diacetonitrile which is used, for example, for preparing pharmaceutical active compounds; additional, technically complicated purification steps are necessary.

Surprisingly, we have now found such a process for preparing diacetonitrile as has short reactions, as is free of the danger of unconverted sodium being left over, and as produces diacetonitrile without recrystallizing in a purity of above 99.5%. This is possible by carrying out the reaction at a temperature which is above the melting point of sodium and by precipitating in cold water the liquid diacetonitrile formed on hydrolyzing the sodium salt and on separating off the aqueous and solvent phases.

The invention accordingly relates to such a process for preparing pure diacetonitrile as comprises reacting acetonitrile with molten sodium at a temperature of 97° to 140° C. and under a pressure of 1 to 10 bar in an inert organic medium which is liquid under the reaction conditions, until the reaction is substantially complete cooling down the mixture to 0°–50° C., hydrolyzing the sodium salt formed by adding water in an amount which is sufficient to dissolve all of the sodium hydroxide and sodium cyanide formed in the hydrolysis, to form a three-phase system from which the aqueous phase and the inert organic medium are separated off, admixing the remaining, third, middle phase, which is crude, liquid diacetonitrile, with 0.5 to 3 times the amount of water, and cooling the mixture down to −10° C. to +30° C., whereupon pure diacetonitrile crystallizes out of the cold mixture and is separated off.

The first reaction step, namely the formation of the sodium salt of diacetonitrile, is carried out by melting sodium in the presence of a liquid medium which is inert to sodium, in a heatable and coolable stirred vessel which is equipped with a reflux condenser and has been flushed beforehand with nitrogen, and adding acetonitrile with constant thorough stirring. The inert liquid medium should advantageously have a boiling point of at least 97° C., which is the melting point of sodium, to about 200° C., a boiling point of up to about 140° C. being usually adequate. Examples of such inert liquid media are aliphatic, cycloaliphatic and aromatic hydrocarbons, for example gasolines having the corresponding boiling range, decalins, toluene or mixtures of these solvents.

The reaction is carried out at a temperature of 97°–140° C., preferably at 100°–120° C., the temperature range up to 110° C. being particularly preferred. The reaction is carried out under atmospheric pressure or, in particular if hydrocarbons having relatively low boiling points are used, under elevated pressures which correspond to the vapor pressures of the solvents at the chosen reaction temperature. The pressure is 1–10 bar, preferably 2–5 bar.

The acetonitrile added reacts virtually instantaneously, so that the amount which vaporizes and has to be condensed in the reflux condenser is small. It is advantageous to introduce the acetonitrile below the surface of the reaction mixture, preferably at the floor of the reaction vessel.

The rate of reaction is extremely high under the conditions mentioned and is, in practice, only limited by the rate at which the heat of reaction can be conducted away and hence only by the type of the reactor. The methane formed in accordance with the reaction equation is continuously blown off.

Since all of the sodium is converted in the reaction, only the theoretically necessary amount of acetonitrile is needed for the conversion. Depending on how the reaction is controlled, small amounts of acetonitrile condense in the condenser and are returned into the reaction until the theoretical amount of acetonitrile has been consumed. It is also possible to carry out the reaction with a small, approximately 10%, excess, and, at the end of the reaction, to distil off the acetonitrile through the condenser since the temperature of the reaction mixture is anyhow significantly above the boiling point of acetonitrile. If the solvents used have a boiling point which is not significantly above that of acetonitrile, fractions of this solvent can also be distilled off, together with the acetonitrile. At any rate, the distillate can be used for a subsequent batch.

The suspension is cooled down and admixed at temperatures of 0°–50° C., preferably at 15°–35°, with sufficient water to hydrolyze the sodium salt of diacetonitrile to free diacetonitrile and to bring the resulting sodium hydroxide and the sodium cyanide formed in the first reaction step into an aqueous solution. The amount of water is accordingly chosen to be sufficient to decompose all of the sodium salt and to bring all of the sodium hydroxide and sodium cyanide into solution. About 1–1.5 parts by weight of water are required per part by weight of acetonitrile used.

Since diacetonitrile is slightly soluble in water, the sodium salt is preferably decomposed by means of the centrifuge mother liquor obtained in the later crystallization step. Since the reaction proceeds virtually without any troublesome side reactions, only a small part of the mother liquor has to be flushed away to dispose of byproducts.

Since all of the sodium is consumed if the procedure of the invention is followed, the water can be added rapidly and without special precautions, the sole time-determining factor being the fact that to maintain the abovementioned temperature limit the heat of reaction or solution has to be conducted away.

Three phases are present after the decomposition. The top phase consists of the inert organic solvent and is separated off and can be returned again and again into the first stage, since it is free of byproducts. The bottom layer, an aqueous solution of sodium hydroxide and sodium cyanide, is separated off. The middle layer, which consists of liquid diacetonitrile, a little water and small amounts of dissolved salts, is admixed with cold water and cooled down with efficient stirring to temperatures of about −10° to +30° C., preferably to temperatures of −8° to +5° C. The amount of water added should be about 0.5 to 3 times the likely amount of diacetonitrile, preferably about twice the amount. On adding the water, diacetonitrile crystallizes out in the form of pure, coarsely grained crystals, and is separated off by filtration or centrifugation, and dried. The centrifugemoist, coarsely crystalline product astonishingly contains only a few percent of water, and mild drying at 35°–40° C. in vacuo rapidly lowers the water content to below 0.2%.

The centrifuge mother liquor, which, due to the fact that diacetonitrile has a certain solubility in water, contains a small amount of diacetonitrile, is preferably used to decompose the sodium salt of diacetonitrile formed in the first reaction step. Using the mother liquor does not impair the purity of the product.

The product prepared in this way is extremely pure, the diacetonitrile content being above 99.5%, and needs not be recrystallized.

The 4-amino-2,6-dimethylpyrimidine (kyanmethin) content is less than 0.1%, the NaCN content is less than 0.05%, and 5-amino-4-cyano-3-methyl-2,4-hexadienenitrile could not be detected.

EXAMPLE 1

(a) 92 g of sodium (4 moles) are introduced together with 700 ml of gasoline (boiling range: 100°–140° C.) into a reactor which is equipped with a stirrer and has been inertized with nitrogen, and the mixture is heated to 105° C. 265 g of acetonitrile (6.5 moles) are continuously added, while the reaction temperature is maintained at about 110° C. by conducting away the heat. A pressure of 3–5 bar is maintained in the reactor, and methane is blown off throughout the entire length of reaction. The addition of acetonitrile is complete after 20 minutes. Following a brief, 25 minute period of further reaction, the reactor is let down, and the excess acetonitrile is distilled off.

The reaction mixture is cooled down to 30°–40° C. and added, with stirring, to 290 ml of water. The temperature is maintained at a constant value by conducting the heat away, and the addition is complete after 10 minutes. The three resulting phases are then separated. The middle, oily phase, which contains the diacetonitrile, is admixed with 200 ml of water and cooled down, with stirring, to below 0° C. The mixture is seeded with a few diacetonitrile crystals, and the product crystallizes out in coarse, white to pale yellow crystals which are isolated by centrifugation and are dried.

| | |
|---|---|
| Yield: | 81.7% |
| Content: | 99.5% |
| 4-amino-2,6-dimethyl-pyrimidine (from gc): | less than 0.1% |
| NaCN: | less than 0.05% |
| H$_2$O: | about 0.2% |
| 5-amino-4-cyano-3-methyl-2,4-hexadiene-nitrile (from gc): | not detectable |

(b) A second batch is carried out with the same amounts and under the same conditions, except that the acetonitrile recovered from the first batch and the gasoline obtained in the phase separation are used in the reaction together with fresh starting materials. Furthermore, the mother liquor obtained on centrifuging the first batch is used to decompose the sodium salt.

(c) Procedure (b) is repeated three more times and then assessed. An experiment produces on average 151 g of diacetonitrile (hardly colored, and crystalline) having a purity of 99.5%; this corresponds to a yield of 92.0% of theory.

EXAMPLE 2

92 g of sodium are introduced into a heatable reactor which is equipped with a stirrer and has been inertized with nitrogen, the sodium is covered with 1,300 ml of decalin, and the mixture is raised to 100° C. When this temperature has been reached, acetonitrile is introduced by means of a metering pump through a dip tube extending to the bottom of the reactor. The unconverted acetonitrile vapor is condensed by means of a condenser and is returned into the reactor via the metering pump. This procedure is carried out until the theoretical amount of acetonitrile, namely 247 g, has been consumed. This is the case after about 50 minutes.

When the supply of acetonitrile is complete, the suspension is cooled down and is then hydrolyzed at about 30° C. by adding, with stirring, 300 ml of water, the water phase containing sodium cyanide is separated off, and the decalin and oil phases are jointly washed with efficient stirring with 100 ml of water. The oil phase, which contains the diacetonitrile, is then separated off and stirred into 200 ml of water, some diacetonitrile crystals are added, and the diacetonitrile crystallizes out at a temperature of less than 0° C., and the mixture is centrifuged. This gives 149 g of diacetonitrile having a purity of 99.5%. To improve the yield further it is possible to use the wash water for decomposing the sodium salt of a subsequent batch and to use the centrifuge mother liquor, instead of pure water, to crystallize subsequent batches.

EXAMPLE 3

16 kg of sodium are melted together with 140 liters of gasoline (boiling point: 100°-140° C.) in a stirred vessel which has been inertized with nitrogen. 47 kg of acetonitrile (10% excess) are then added with continuous stirring at a temperature of 100°-110° C. and under a pressure of 3-5 bar in the course of 40 minutes, during which the methane formed is continuously blown off, and the reaction heat is conducted away by constant cooling. The excess acetonitrile is stripped off, and the suspension is cooled down to 30°-40° C. and is hydrolyzed at 30°-40° C. in the course of 15 minutes with 52 liters of water. The resulting three-phase mixture is separated into an aqueous, NaOH- and NaCN-containing layer, a gasoline layer, and the middle, oil layer, which contains diacetonitrile and is admixed with 35 liters of water at a temperature of about −4° to 0° C. The white, coarsely crystalline diacetonitrile precipitate is centrifuged off, briefly washed and dried at 35°-40° C. in vacuo.

The experiment is repeated five times, the gasoline being replenished each time to the full, and in each case about 90% of the centrifuge mother liquor and the wash water are used to decompose the sodium salt of diacetonitrile. The yield per experiment is 26 kg, which corresponds to 91% of theory.

| Analysis: | | |
|---|---|---|
| | Diacetonitrile: | 99.7% |
| | Kyanmethin from GC: | less than 0.1% |
| | NaCN: | less than 0.05% |
| | $H_2O$: | about 0.2% |
| | 5-amino-4-cyano-3-methyl-2,4-hexadienenitrile (from GC): | not detectable |

What I claim is:

1. A process for preparing pure diacetonitrile, which comprises reacting acetonitrile with molten sodium at a temperature of 97° to 140° C. and under a pressure of 1 to 10 bar in an inert organic medium which is liquid under the reaction conditions, until the reaction is substantially complete, cooling down the mixture to 0°-50° C., hydrolyzing the sodium salt formed by adding water in an amount which is sufficient to dissolve all of the sodium hydroxide and sodium cyanide formed in the hydrolysis, to form a three-phase system from which the aqueous phase and the inert organic medium are separated off, admixing the remaining, third, middle phase, which is crude, liquid diacetonitrile, with 0.5 to 3 times the amount of water, and cooling the mixture down to −10° C. to +30° C., whereupon pure diacetonitrile crystallizes out of the cold mixture and is separated off.

2. The process claimed in claim 1, wherein the reaction of acetonitrile with sodium is carried out at a temperature of 100°-115° C.

3. The process claimed in claim 1, wherein the reaction of acetonitrile with sodium is carried out under a pressure of 2-5 bar.

4. The process claimed in claim 1, wherein the aqueous mother liquor remaining after the crystallized diacetonitrile has been crystallized out is returned into the process to use it to hydrolyze the sodium salt formed in the reaction between acetonitrile and sodium.

5. The process claimed in claim 1, wherein, after the separation, the inert organic medium is used for a further reaction with sodium.

6. The process claimed in claim 1, wherein the diacetonitrile is allowed to crystallize out at a temperature of −5° C. to +5° C.

* * * * *